Figure 1:
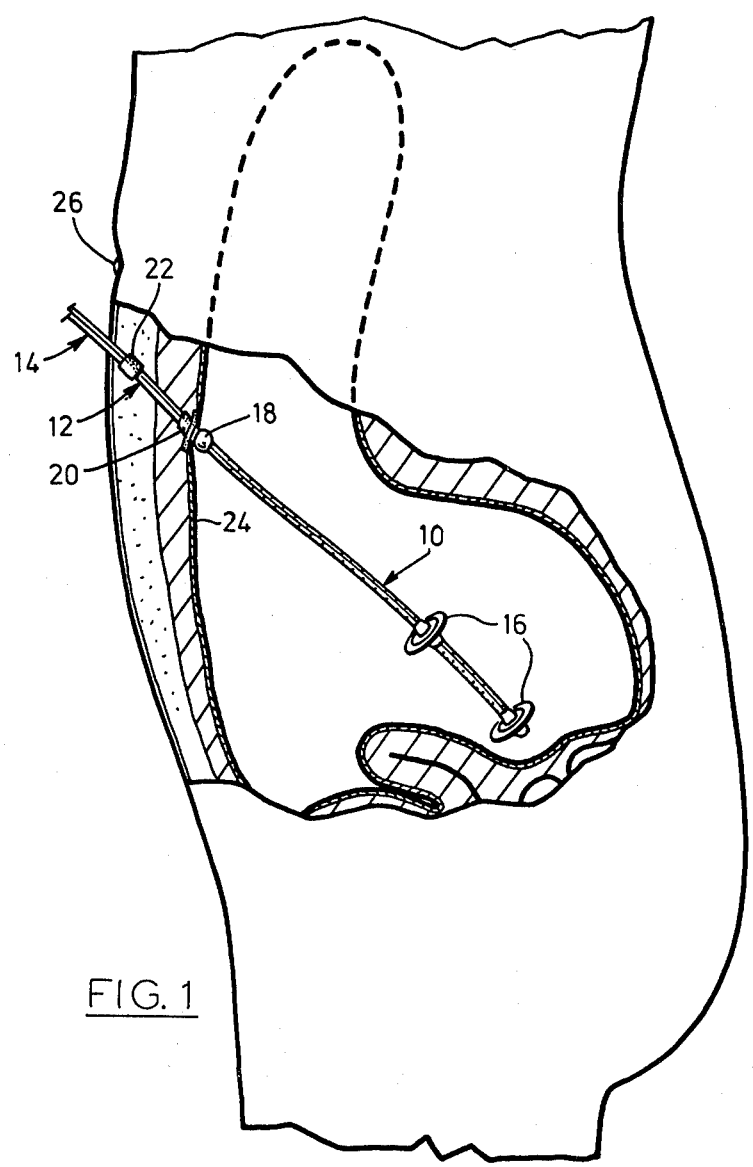
Figure 2:
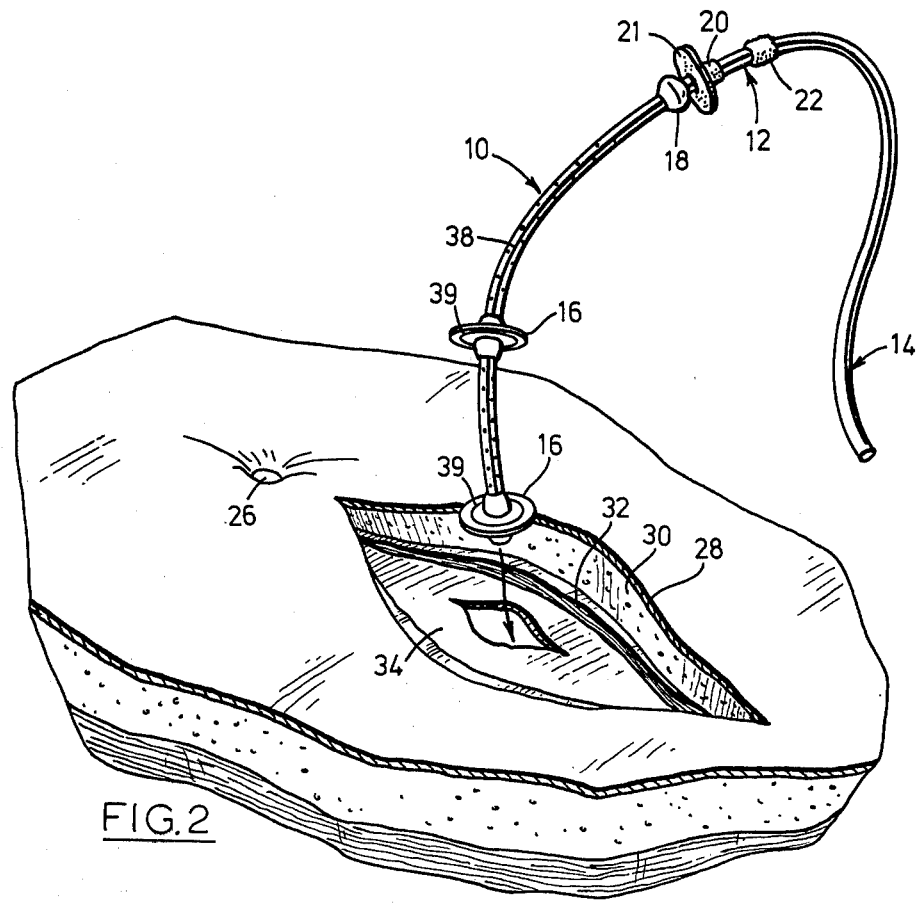

United States Patent [19]

Oreopoulos et al.

[11] 4,392,855
[45] Jul. 12, 1983

[54] CATHETER

[76] Inventors: Dimitrios G. Oreopoulos, 10 Ladywood Dr., Rexdale, Ontario; Gabor Zellerman, 566-590 Richmond Street West, Toronto, Ontario, both of Canada

[21] Appl. No.: 253,948

[22] Filed: Apr. 14, 1981

[51] Int. Cl.³ .............................................. A61M 25/00
[52] U.S. Cl. ...................................... 604/175; 604/29; 604/280
[58] Field of Search .................... 128/214 R, 348–350, 128/213 A; 604/29, 280, 175

[56] References Cited

U.S. PATENT DOCUMENTS

| 3,516,410 | 6/1970 | Hakim | 128/350 R |
| 3,633,585 | 1/1972 | McDonald | 128/348 |
| 3,853,126 | 12/1974 | Schulte | 128/348 X |
| 4,184,497 | 1/1980 | Kolff et al. | 128/213 A |
| 4,278,092 | 7/1981 | Borsanyi et al. | 128/348 |

OTHER PUBLICATIONS

Gaertner-Surgery, Gynecol. & Obstet., Sep. 1964, vol. 119, #3, pp. 599–600.

Primary Examiner—Dalton L. Truluck
Attorney, Agent, or Firm—Fetherstonhaugh & Co.

[57] ABSTRACT

The invention is a permanent catheter for use in the practice of peritoneal dialysis. It has a bead on the tube that, in use, underlies the peritoneum and a cuff made of a fibrous material that has a disc that overlies the peritoneum and forms a scar tissue as a seal.

1 Claim, 6 Drawing Figures

CATHETER

This invention relates to a permanent catheter for use in the practice of peritoneal dialysis.

In the practice of peritoneal dialysis a dialysate is admitted to the peritoneal cavity of the patient through a permanent peritoneal catheter. These catheters have a perforate peritoneum section within the peritoneal cavity that communicates with an exterior section exterior of the patient's body adjacent the umbilicus. In practice, dialysate is supplied to and drained from the peritoneum through the permanently implanted catheter.

These catheters are inserted in a surgical operation. They are generally satisfactory, but complications in their use are encountered. Among the complications are fibrin clot formation and skin infection at the place of exit of the catheter from the skin and fluid leak at the place of entry to the peritoneal cavity. It is an object of this invention to provide a means in such a catheter that will in use permit the achievement of a more positive seal at the point of entry to the peritoneum with a view to avoiding leakage and drainage problems encountered not infrequently with catheters according to existing practice.

With this and other objects in view a peritoneal catheter according to the present invention is made of flexible tubing and comprises a continuous flexible tube having a peforated peritoneum section, a subcutaneous section and an exterior section; the peritoneum section having a circumferentially extending bead of inert material adjacent the subcutaneous section and a fibrous peritoneum cuff adjacent the bead; the subcutaneous section having means for sealing the catheter at the outer skin. The invention will be clearly understood after reference to the following detailed specification read in conjunction with the drawings.

In the drawings:

FIG. 1 is a sectional view of the lower abdomen of a patient showing the general disposition of a permanent catheter in a patient;

FIGS. 2 to 6 inclusive are illustrations illustrating steps of surgical procedure for inserting a catheter according to this invention.

The flexible tubing of the catheter illustrated in the drawings is made from an inert plastics material such as a silastic material and has a perforate peritoneum section 10, a subcutaneous section 12 and an exterior section 14. The peritoneum section 10 has spaced apart flexible locating discs 16. The peritoneum section also has a bead 18 adjacent the subcutaneous section preferably made of the same material as the tubing which in use cooperates with a closely spaced peritoneum felted fibrin cuff 20. A subcutaneous cuff 22 is mounted on the subcutaneous section 12 adjacent the exterior section 14.

The use of dacron, or similar material, felted cuffs such as the cuffs 20 and 22 which integrate with body tissue to form a scar tissue to seal the catheter at its point of entry through the skin or membrane is not new in permanent catheter practice. Their use is common and beneficial, but as noted in the preamble to this specification their use does leave something to be desired in the achievement of a seal that is relatively fluid leakage free. Fluid leak is, of course, a common source of inflamation.

This invention is concerned with the external bead 18 on the catheter that in use is located on the inside of the peritoneal membrane and cooperates with an outwardly spaced felt cuff 20 in the positive locating and securement of the catheter at the membrane. FIG. 1 shows the catheter in place. It will be noted that the peritoneum section 10 extends downwardly from its point of entry through the peritoneum membrane 24 to the pelvic area. The discs 16 are made from a flexible plastics material similar to the catheter tube and serve to permanently located the catheter in this position. It will be understood that the peritoneal cavity is occupied by the intestines and other organs of the body. These discs interlock with the organs and serve to anchor the catheter in its location. Displacement of catheters is a concern and these discs do assist in positively locating the catheter, but they do not form part of the present invention.

The seal of the catheter at the peritoneum membrane 24 is achieved by the bead 18 and the cuff 20 outwardly of the bead Cuff 20 preferably has a radially extending disc 21. Bead 18 is on the inner side of the membrane while the cuff 20 and its disc 21 is on the outer side of the membrane. As healing occurs the cuff forms a scab tissue with the muscle fibre on the outside of the peritoneal cavity.

The seal at the skin is achieved by the cuff 22 at a location preferably just below the umbilicus 26.

Figure 3:
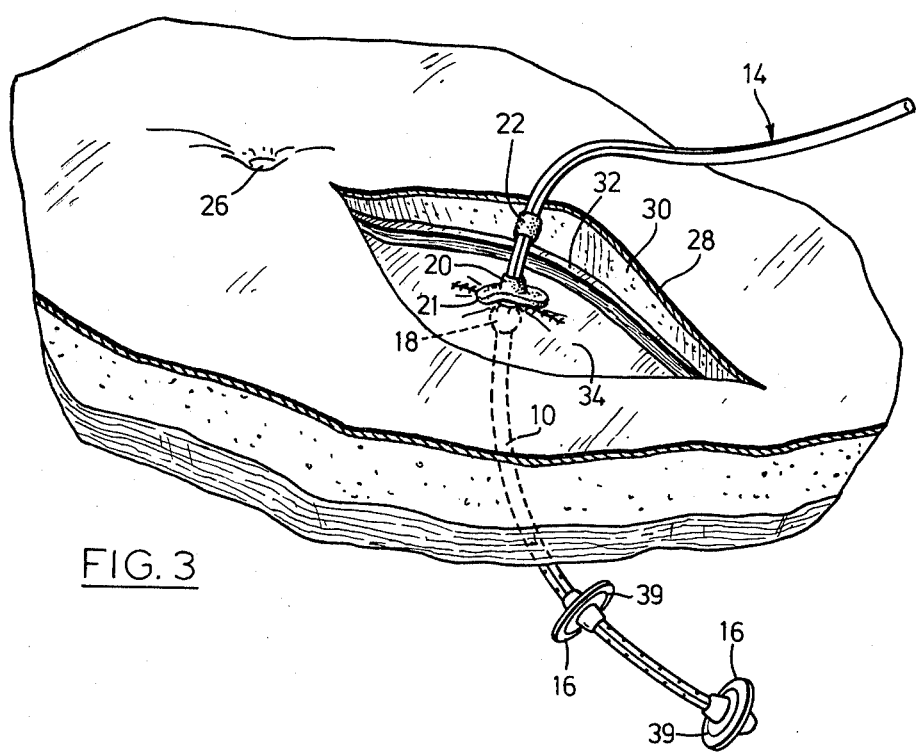

As illustrated in FIG. 1, the first step is to make a short mid-line infra-umbilical incision through the skin 28, body fat 30 and muscle 32. A smaller incision is made through the peritoneal membrane 34. The peritoneum section of the catheter is inserted through the smaller incision in the peritoneal membrane and directed into the pelvic area to assume a position illustrated in FIG. 1. The bead 18 is located within the peritoneal cavity immediately under the peritoneal or peritoneum membrane and the peritoneum incision is sutured. The cuff 20 overlies the sutured peritoneum membrane and the incision through the muscle layer 32 is then sutured as illustrated in FIG. 3. The muscle layer is caused to overlie the felt cuff 20 and its disc 21.

Figure 4:
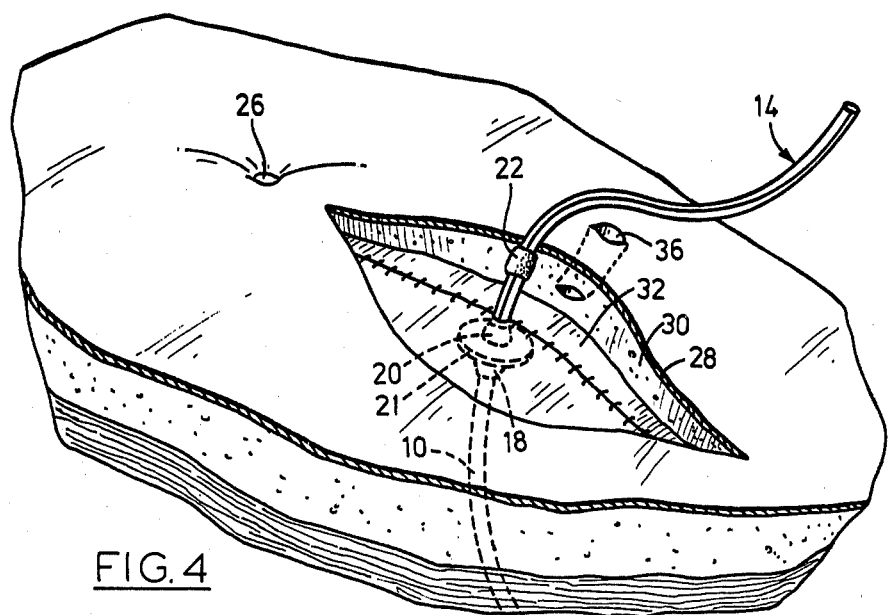
Figure 5:
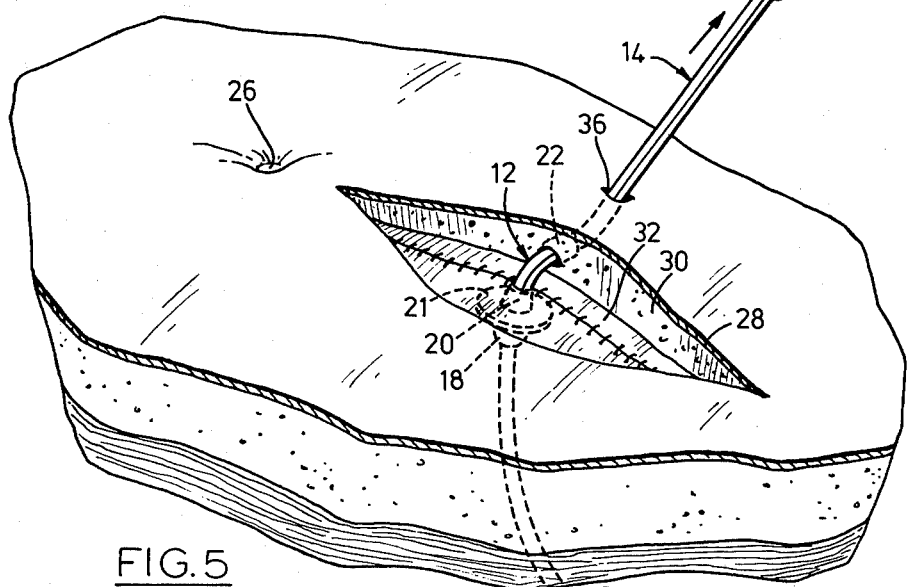
Figure 6:
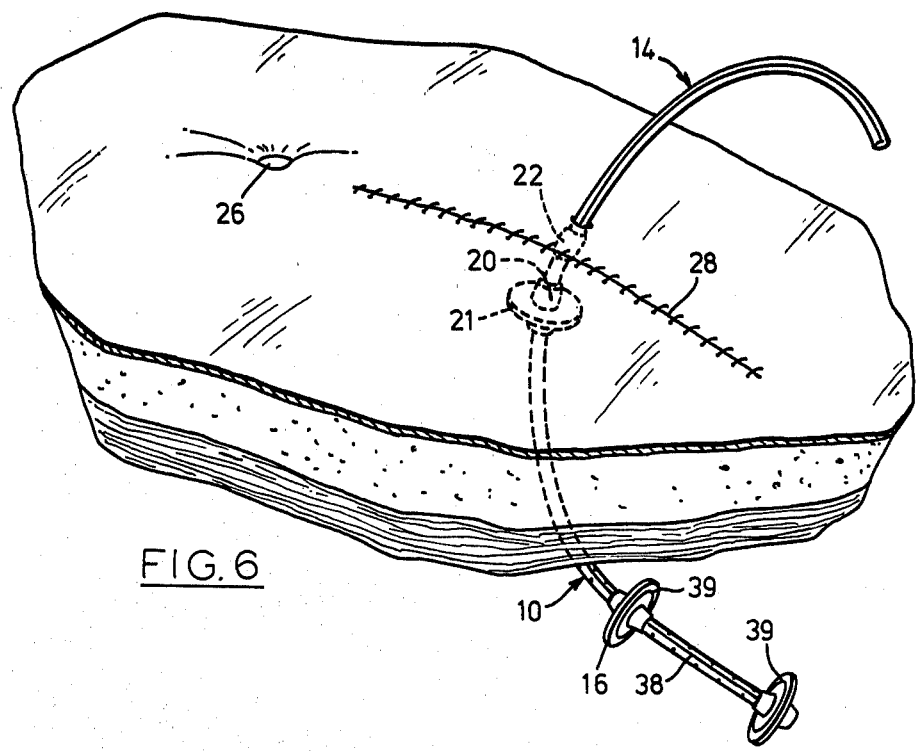

A small incision is then made in the skin adjacent the edge of the incision as illustrated at numeral 36 and the free end of the catheter is pulled through the skin opening as illustrated in FIG. 4. The incision in the skin is then sutured as illustrated in FIG. 5 with the felt cuff 22 about 1 cm from the surface of the skin.

It will be appreciated that the insertion procedure will vary from surgeon to surgeon. The foregoing has been merely indicated as an outline of one possible surgical procedure.

In use, it has been found that the combination of the bead and the cuff provide an effective method for installing the catheter in a secure way that achieves a more positive seal at the peritoneum membrane than the existing practice of using a cuff per se. Preferably the cuff has a disc as illustrated and the disc on the cuff is thought to be new.

The catheter preferably carries a stripe 38 of a radiopaque material and the locating discs 16 carry a strip of radiopaque material so that the location of the catheter and the discs can be determined by X-ray. Futher, the bead 18 is also preferably radiopaque. It is often useful to be able to positively locate the point of entry of the catheter through the peritoneal membrane because this also locates the membrane. A radiopaque bead is useful in this respect.

Embodiments and modifications in the invention will be apparent to those skilled in the art. Cuffs and catheters are generally well known and specifications of cuff materials and catheter materials are well known. A selection is available in the art and this invention is not restricted to any or other of them.

The embodiments of the invention in which an exclusive property or privilege is claimed are defined as follows:

1. A permanent peritoneal catheter of flexible tubing comrpising a continuous flexible tube having a perforate peritoneum section, a subcutaneous section and an exterior section;

said peritoneum section having flexible locating discs of inert plastics material extending therefrom;

the peritoneum section having a circumferentially extending bead of inert material adjacent the subcutaneous section and a fibrous peritoneum cuff outwardly of and close to the bead;

said fibrous peritoneum cuff having a fibrous disc extending radially therefrom;

said fibrous peritoneum cuff and fibrous disc being close to said bead as aforesaid whereby to cooperate with said bead to hold a peritoneum membrane therebetween and form a seal at the peritoneum membrane in use;

the subcutaneous section having means for sealing the catheter at the outer skin.

* * * * *